United States Patent [19]

Van Gilse et al.

[11] 4,286,983
[45] Sep. 1, 1981

[54] ALGICIDAL COMPOSITION AND METHOD OF PREVENTING OR CONTROLLING ALGAE WITH SAID COMPOSITION

[75] Inventors: Jaap Van Gilse; Gerard B. Paerels, both of Weesp, Netherlands

[73] Assignee: Duphar International Research B.V., Netherlands

[21] Appl. No.: 59,420

[22] Filed: Jul. 20, 1979

[30] Foreign Application Priority Data

Jul. 26, 1978 [NL] Netherlands ........................ 7807908

[51] Int. Cl.$^3$ ............................................ A01N 33/06
[52] U.S. Cl. .......................................... 71/67; 71/121; 564/367; 564/368
[58] Field of Search ............................................ 71/67

[56] References Cited

U.S. PATENT DOCUMENTS

| | | | |
|---|---|---|---|
| 2,830,056 | 4/1958 | Ruschig et al. | 544/392 |
| 3,173,917 | 3/1965 | Starker et al. | 544/392 |
| 3,394,137 | 7/1968 | Morris | 71/67 |
| 3,871,861 | 3/1975 | Merianos et al. | 71/67 |

Primary Examiner—Paul M. Coughlan, Jr.

Attorney, Agent, or Firm—Stevens, Davis, Miller & Mosher

[57] ABSTRACT

Algicidal composition comprising in an algicidally effective amount a diamine of the formula

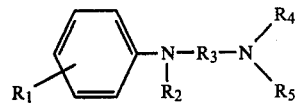

wherein $R_1$ is hydrogen or up to three substituents such as halogen, alkyl, phenoxy, phenylthio, or halogen substituted alkoxy, $R_2$ is hydrogen or a substituent such as alkyl, phenyl, halogen substituted phenyl or a trifluoromethyl-substituted phenyl group, $R_3$ is an alkylene of 2 to 6 carbon atoms, $R_4$ is hydrogen or alkyl of 1 to 4 carbon atoms, $R_5$ is alkyl of 1 to 6 carbon atoms or $R_4$ and $R_5$ are together tetramethylene or pentamethylene or $R_2$ and $R_5$ are together ethylene and where $R_1$ is other than three halogen atoms.

6 Claims, 40 Drawing Figures

ALGICIDAL COMPOSITION AND METHOD OF PREVENTING OR CONTROLLING ALGAE WITH SAID COMPOSITION

The invention relates to an algicidal composition and to the prevention or control of algae with said composition. The invention also relates to new diamines and to the preparation of said compounds.

Undesired growth of algae is an ever increasing phenomenon in surface waters, such as irrigation canals and drainage canals, fish-ponds, wet rice-fields, and the like. The quality or the flow of the water can be very detrimentally influenced by said growth of algae, as well as, as in the last example, the growth of the crop. Algae can also adhere to walls which are in contact with water, for example ship's skins and wooden campshots. As a result of this a more frequent maintenance of the walls becomes necessary; in addition the algae limit the speed of the ship. Consequently an agent to prevent or to control algae is of great importance.

When applied to surface water, such an agent, however, should satisfy very stringent environmental requirements because only the growth of algae in the water is to be controlled, but the evolution of other organisms living in the water may not be detrimentally influenced. The choice of a suitable algicide hence is much more critical than, for example, that of a herbicide because in the concentration used toxicity with respect to other forms of living in the water should be entirely absent.

Netherlands Patent Application No. 68 18056 relates to algicidal compositions containing a diamine, for example N-(2,4,5-trichlorophenyl)-ethylenediamine as an active compound. However, this compound proves to be so toxic with respect to various organisms living in the water that the substance is not to be considered for controlling algae in surface water.

Figure 1:
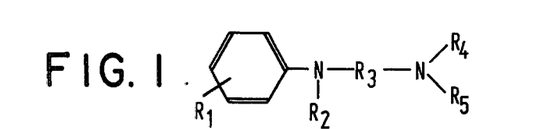

It has now been surprisingly found that undersired growth of algae can effectively be controlled without damaging the environment by using a composition which, in addition to a solid or liquid carrier material, comprises a compound of the general formula of FIG. 1, wherein $R_1$ represents from 0 to 3 substituents selected from the group consisting of a halogen atom, an optionally halogen-substituted alkyl group having from 1 to 16 carbon atoms, a cycloalkyl group having 5 or 6 carbon atoms, an optionally halogen-substituted alkoxy group, alkylthio group or alkylsulfonyl group having from 1 to 4 carbon atoms, and a phenoxy group, phenylthio group or $C_7$-$C_9$ phenylalkyl group which, if desired, is substituted with halogen or with an optionally fluorine-substituted alkyl group having from 1 to 4 carbon atoms, or
wherein $R_1$ and the attached phenyl group together constitute a naphthyl group,
wherein $R_2$ is a hydrogen atom, an alkyl group having from 1 to 4 carbon atoms, or an optionally halogen-substituted or trifluoromethyl-substituted phenyl group,
$R_3$ is an optionally branched alkylene group having from 2 to 6 carbon atoms,
$R_4$ is a hydrogen atom or an alkyl group having from 1 to 4 carbon atoms, and
$R_5$ is an alkyl group having from 1 to 6 carbon atoms, or wherein $R_4$ and $R_5$ together constitute a tetramethylene group or pentamethylene group, or wherein $R_2$ and $R_5$ together constitute an ethylene group, or a salt of this compound, with the proviso that $R_1$ does not represent three halogen atoms.

Figure 2:
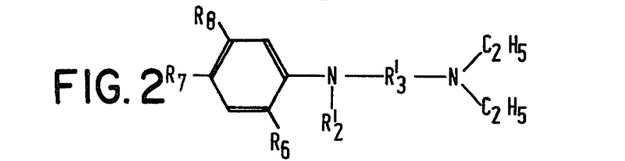

Suitable in particular for this application are compositions which comprise as an algicidally active substance a compound of the general formula of FIG. 2, wherein
$R'_2$ is a hydrogen atom, a methyl group or a phenyl group,
$R'_3$ is an ethylene group, trimethylene group or 2-methylethylene group,
$R_6$ and $R_8$ are equal or different and represent hydrogen atoms, chlorine atoms or methyl groups,
$R_7$ is a chlorine atome or a methyl group, and wherein, if $R_6$ and $R_8$ both represent hydrogen atoms,
$R_7$ is in addition a trifluoromethyl group, an n-alkyl group having from 2 to 10 carbon atoms or a cyclohexyl group,
or a salt of this compound,
with the proviso that not both $R_6$ and $R_7$ and $R_8$ are chlorine atoms, and
with the proviso that, if $R_6$ and $R_8$ both are hydrogen atoms and $R_7$ is a chlorine atom, $R'_3$ is an ethylene group.

Figures 3, 4:
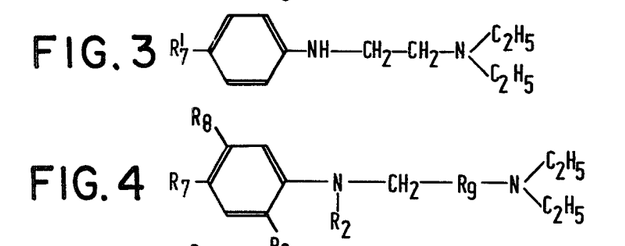

Of the last-mentioned active substance are most effective, compounds of the general formula of FIG. 3, wherein $R'_7$ is a trifluoromethyl group, n-butyl group or cyclohexyl group.

Examples of compounds having a high algicidal activity are:

(1) N-(4-chlorophenyl)-N',N'-diethyl-ethylene diamine,
(2) N-(3,4-dichlorophenyl)-N',N'-diethyl-ethylene diamine,
(3) N-(3,4-dichlorophenyl)-N',N'-diethyl-trimethylene diamine,
(4) N-(3,4-dichlorophenyl)-N-methyl-N',N'-diethyl-ethylene diamine,
(5) N-(4-chlorophenyl)-N-methyl-N',N'-diethyl-ethylene diamine,
(6) N-(4-trifluoromethylphenyl)-N',N'-diethyl-ethylene diamine,
(7) N-(4-trifluoromethylphenyl)-N',N'-diethyl-trimethylene diamine,
(8) N-(4-n-butylphenyl)-N',N'-diethyl-ethylene diamine,
(9) N-(4-chlorophenyl)-N-phenyl-N',N'-diethyl-ethylene diamine,
(10) N,N-diethyl 2-(3,4-dichloroanilino)propylamine,
(11) N-(4-n-butylphenyl)-N',N'-diethyl-trimethylene diamine,
(12) N-(3,4-dichlorophenyl)-N-methyl-N',N'-diethyl-trimethylene diamine,
(13) N-(3-chloro-4-methylphenyl)-N',N'-diethyl-ethylene diamine,
(14) N-(4-cyclohexylphenyl)-N',N'-diethyl-ethylene diamine,
(15) N-(4-n-propylphenyl)-N',N'-diethyl-ethylene diamine,
(16) N-(4-n-nonylphenyl)-N',N'-diethyl-ethylene diamine,
(17) N-(2,4,5-trimethylphenyl)-N',N'-diethyl-ethylene diamine,
(18) N-(2,4-dichlorophenyl)-N',N'-diethyl-ethylene diamine,
(19) N-(4-cyclohexylphenyl)-N',N'-diethyl-trimethylene diamine and salts of these compounds.

Of these active substances, compounds (3), (6), (7) and (17) are excellently suitable because in these compounds a very strong algicidal activity is associated with a very low toxicity with respect to other organisms living in the water.

Examples of active substances which may also be used successively in algicidal compositions are:

(20) N-[4-{2-(4-chlorophenyl)ethyl}phenyl]-N'-N'-diethylethylene diamine,
(21) N-[4-{2-(4-chlorophenyl)ethyl}phenyl]-N',N'-diethyltrimethylene diamine,
(22) N-(3,4-dichlorophenyl)-N'-tert.butyl-ethylene diamine,
(23) N-(3,4-dichlorophenyl)-N'-isopropyl-ethylene diamine,
(24) N-phenyl-N',N'-diethyl-ethylene diamine,
(25) N-[4-(4-chlorophenoxy)phenyl]-N',N'-diethylethylene diamine,
(26) N-(3-chlorophenyl)-N',N'-diethyl-ethylene diamine,
(27) N-(4-chlorophenyl)-N'-methyl-N'-n-butyl-ethylene diamine,
(28) N-(4-chlorophenyl) 2-piperidylethyl amine,
(29) N-(4-bromophenyl)-N',N'-diethyl-ethylene diamine,
(30) N-(3-trifluoromethylphenyl)-N',N'-diethyl-ethylene diamine,
(31) N-(4-chlorophenyl)-N',N'-dimethyl-ethylene diamine,
(32) N-(3,4-dichlorophenyl)-N'-ethyl-ethylene diamine,
(33) N-phenyl-N-methyl-N',N'-diethyl-ethylene diamine,
(34) N,N-diethyl-2-(4-chloroanilino)isopropyl amine,
(35) N,N-diethyl 2-(3,4-dichloroanilino)isopropyl amine,
(36) N,N-diethyl 2-(4-chloroanilino)propylamine,
(37) N-(4-chlorophenyl)-N',N'-diethyl-trimethylene diamine,
(38) N-(4-chlorophenyl)-N-ethyl-N',N'-diethyl-ethylene diamine,
(39) N-(4-chlorophenyl)-N-isopropyl-N',N'-diethylethylene diamine,
(40) N-(4-chlorophenyl)-N-isopropyl-N',N'-diethyltrimethylene diamine,
(41) N-(4-methylphenyl)-N',N'-diethyl-ethylene diamine,
(42) N-(2,4-dimethylphenyl)-N',N'-diethyl-ethylene diamine,
(43) N-(1-naphthyl)-N',N'-diethyl-ethylene diamine,
(44) N-(2,4-dimethylphenyl)-N',N'-diethyl-trimethylene diamine,
(45) N-(3-chloro-4-fluorophenyl)-N',N'-diethyl-ethylene diamine,
(46) N-(4-chlorophenyl)-N',N'-diethyl-pentamethylene diamine,
(47) N-(4-trifluoromethoxyphenyl)-N',N'-diethyl-ethylene diamine,
(48) N-(4-trifluoromethylsulfonylphenyl)-N',N'-diethyl-ethylene diamine,
(49) N-(4-chlorophenyl)-N'-ethyl-piperazine,
(50) N-(3-chloro-4-(fluorophenyl)-N',N'-diethyltrimethylene diamine,
(51) N-(4-n-hexylphenyl)-N',N'-diethyl-ethylene diamine,
(52) N-(4-tert.butylphenyl)-N',N'-diethyl-ethylene diamine,
(53) N-(4-chlorophenyl)-N-ethyl-N',N'-diethyl trimethylene diamine,
(54) N-(4-n-heptylphenyl)-N',N'-diethyl-ethylene diamine,
(55) N-(4-n-octylphenyl)-N',N'-diethyl-ethylene diamine, and salts of these compounds.

As will become apparent from the examples, growth of algae is prevented by the compositions according to the invention or the algae are efficiently killed. At the concentration at which a satisfactory algicidal activity is found, no toxicity is observed with respect to other living organisms in the water, such as fish.

The algicidal compositions according to the invention are suitable for preventing or controlling all kinds of algae, such as Vaucheria, Cladophora, Mougeotia, Hydrodiction, Spirogyra, Eudogonium sp. and Enteromorpha. The dosage suitable for application will depend inter alia on the kind and population density of the algae to be controlled, and also on the conditions of the water, such as temperature, flow, pH and hardness, and on the soil conditions.

In the compositions according to the invention the active substance is mixed with solid carrier material or dissolved or dispersed in liquid carrier material, possibly in combination with auxiliary substances, such as emulsifiers, dispersion agents and stabilisers.

Examples of compositions according to the invention are aqueous solutions and dispersions, solutions in organic solvents, dispersible powders, pastes, miscible oils, granules and pellets. Dispersible powders, pastes and miscible oils are compositions in concentrate form which are diluted prior to or during use.

Some forms of compositions will be explained in detail hereinafter by way of example.

Granular compositions are prepared, for example, by taking up the active substance in a solvent or dispersing it in a diluent and impregnating the resulting solution or suspension, possibly in the presence of a binder, on a granular carrier material. A granular composition may also be manufactured by compressing the active substance in the presence of lubricants and binders, together with powdered minerals and disintegrating the compressed product to the desired grain size and sieving it.

Dispersible powders are prepared by mixing 10 to 80 parts by weight of a solid inert carrier with 10 to 80 parts by weight of the active substance, 1 to 5 parts by weight of a dispersing agent, for example, the lignine sulphonates or alkylnaphthalene sulphonates known for this purpose, and preferably also 0.5 to 5 parts by weight of a wetting agent, for example, fatty alcohol sulphates, alkylarylsulphonates, fatty acid condensation products or polyoxyethylene compounds.

For the preparation of miscible oils the active compound is dissolved in a suitable solvent which is preferably poorly water-miscible and one or usually more emulsifiers is or are added to said solution. The concentration of the active compound in said miscible oils usually varies between 2 and 50 percent, by weight. In addition to a miscible oil may be mentioned as a liquid and highly concentrated primary composition a solution of the active substance in a readily water-miscible liquid, to which solution a dispersing agent and possibly a surfaceactive substance has been added. Upon diluting with water shortly before or during spraying, an aqueous dispersion of the active substance is obtained.

For use in surface water, water-soluble or water-dispersible algicidal compositions are often used or granular compositions c.q. pellets which cause the active substance to dissolve in the water at the desired rate. In order to improve the solubility or dispersibility in water, water-miscible solvents, such as acetone, glycol or glycol ethers may be used, as well as an emulsifier or a mixture of emulsifiers, for example, polyoxyethylene compounds.

For application to walls which are in contact with water ("antifouling") the active substance is taken up in a wall-preservative, for example, a paint, a lacquer or a tar.

Known algicidal and fungicidal compounds may also be incorporated in the compositions according to the invention. As a result of this the activity spectrum of the composition is widened and synergism may occur. To be considered for use in such a combination composition are known algicidal compounds, for example, urea compounds and triazines useful for this purpose and furthermore 7-oxabicyclo(2,2,1)heptane-2,3-dicarboxylic acid and 2-chloro-acetamido-3-chloro-1,4-naphthoquinone. As suitable fungicides may be mentioned:
1. organic tin compounds, for example, triphenyl tin hydroxyde and triphenyl tin acetate;
2. alkylenebisdithiocarbamates, for example zinc ethylenebisdithiocarbamate and manganese ethylenebisdithiocarbamate;
3. 1-acyl- or 1-carbamoyl-N-benzimidazole (-2) carbamates and 1,2-bis(3-alkoxycarbonyl-2-thiureido)benzene;
4. carboxanilides, for example, 5,6-dihydro-2-methyl-1,4-oxathiine-3-carboxanilides, methyl-substituted 5,6-dihydro4H-pyrane-3-carboxanilide and methyl-substituted furane-3-carboxanilide and furthermore 2,4-dinitro-6-(2-octylphenyl)crotonate, 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)tetrahydrophthalimide, N-dichlorofluoromethylthio-N-phenyl-N',N'-dimethylsulphamide, tetrachloroisophthalonitrile, 2-(4'-thiazolyl)benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidine-methanol, 1-(isopropylcarbamoyl)-3-(3,5-dichlorophenyl)-hydantoine, N-(1,1,2,2-tetrachloroethylthio)-4-cyclohexene-1,2-carboximide, N-trichloromethylmercapto-4-cyclohexene-1,2-dicarboximide, and N-tridecyl-2,6-dimethylmorpholine.

As already stated above, the dosage of the composition according to the invention desired for practical applications will depend on several factors. Generally, however, it holds that favourable results are achieved with a dosage which corresponds to 0.1 to 10 kg of the active substance per hectare of surface water, or 0.05 to 10 mg per liter of water. For application to walls which are in contact with water the active substance is taken up in a wall-preservative in a quantity of 0.2–10% by weight.

A few compounds which may be used in the algicidal compositions according to the invention are known from J. Am. Chem. Soc. 68, 2494 (1946) and J. Org. Chem. 26, 476 (1961). However, these publications do not state any pesticidal activity.

A number of the active substances is new. The invention therefore also relates to new compounds of the general formula of FIG. 4 or 5 wherein $R_9$ is an ethylene group or an ethylidene group, and $R_2$, $R_6$, $R_7$ and $R_8$ have the above meanings, as well as to new compounds of the general formula of FIG. 6 wherein $R''_2$ is an alkyl group having 1 to 4 carbon atoms, or a phenyl group optionally substituted with halogen or trifluoromethyl, and $R_4$, $R_5$, $R_6$, $R_7$ and $R_8$ have the above meanings, as well as to new compounds of the general formula of FIG. 7 wherein $R_6$ has the above meaning, $R''_8$ is a hydrogen atom, a chlorine atom, or a methyl group, with the proviso that, if $R''_8$ is a hydrogen atom or a methyl group, $R''_7$ is a methyl group, and, if $R''_8$ is a chlorine atom, $R''_7$ is a fluorine atom, and wherein, if $R_6$ and $R''_8$ both are hydrogen atoms, $R''_7$ is in addition a trifluoromethyl group, trifluoromethoxy group, or trifluoromethylsulphonyl group, a cyclohexyl group, an alkyl group having from 2 to 10 carbon atoms, a p-chlorophenoxy group or a p-chlorophenylalkyl group having 7 or 8 carbon atoms, and to new compounds of the general formula of FIG. 8, wherein $R'_4$ is a hydrogen atom or a methyl group, $R'_5$ is an alkyl group having from 3 to 6 carbon atoms, and $R'_8$ is a hydrogen atom or a chlorine atom, and to salts of the above compounds.

Examples of new compounds according to the invention are:

N-(3,4-dichlorophenyl)-N',N'-diethyl-trimethylene diamine,
N-(3,4-dichlorophenyl)-N-methyl-N',N'-diethyl-ethylene diamine,
N-(4-chlorophenyl)-N-methyl-N',N'-diethyl-ethylene diamine,
N-(4-trifluoromethylphenyl)-N',N'-diethyl-ethylene diamine,
N-(4-trifluoromethylphenyl)-N',N'-diethyl-trimethylene diamine,
N-(4-n-butylphenyl)-N',N'-diethyl-ethylene diamine,
N-(4-chlorophenyl)-N-phenyl-N',N'-diethyl-ethylene diamine,
N,N-diethyl 2-(3,4-dichloroanilino)propylamine,
N-[4-(4-chlorophenoxy)phenyl]-N',N'-diethyl-ethylene diamine,
N,N-diethyl 2-(4-chloroanilino)isopropylamine,
N,N-diethyl 2-(3,4-dichloroanilino)isopropylamine,
N,N-diethyl 2-(4-chloroanilino)propylamine,
N-(4-chlorophenyl)-N',N'-diethyl-trimethylene diamine,
N-(4-chlorophenyl)-N-ethyl-N',N'-diethyl-ethylene diamine,
N-(4-chlorophenyl)-N-isopropyl-N',N'-diethyl-ethylene diamine,
N-(4-chlorophenyl)-N-isopropyl-N',N'-diethyl-trimethylene diamine,
N-(3,4-dichlorophenyl)-N'-tert.butyl-ethylene diamine. HCl salt,
N-(3,4-dichlorophenyl)-N'-isopropyl-ethylene diamine. HCl salt,
N-(4-chlorophenyl)-N'-methyl-N'-n-butyl-ethylene diamine,
N-(4-n-butylphenyl)-N',N'-diethyl-trimethylene diamine,
N-(3,4-dichlorophenyl)-N-methyl-N',N'-diethyl-trimethylene diamine,
N-(4-cyclohexylphenyl)-N',N'-diethyl-ethylene diamine,
N-(4-n-propylphenyl)-N',N'-diethyl-ethylene diamine,
N-(4-n-nonylphenyl)-N',N'-diethyl-ethylene diamine,
N-(2,4,5-trimethylphenyl)-N',N'-diethyl-ethylene diamine,
N-(4-cyclohexylphenyl)-N',N'-diethyl-trimethylene diamine,
N-[4-{2-(4-chlorophenyl)ethyl}phenyl]-N',N'-diethyl-ethylene diamine, N-[4-{2-(4-chlorophenyl)ethyl}phenyl]-N',N'-diethyl-trimetylene diamine, N-(2,4-dimethylphenyl)-N',N'-diethyl-ethylene diamine, N-(2,4-dimethylphenyl)-N',N'-diethyl-trimethylene diamine, N-(4-trifluoromethoxyphenyl)-N',N'-diethyl-ethylene diamine, N-(4-trifluoromethylsulphonylphenyl)-N',N'-diethyl-ethylene diamine, N-(3-chloro-4-fluorophenyl)-N',N'-diethyl-trimethylene diamine, N-(4-n-hexylphenyl)-N',N'-diethyl-ethylene diamine, N-(4-tert.butylphenyl)-N',N'-diethyl-ethylene diamine, N-(4-chlorophenyl)-N-ethyl-N',N'-diethyl-trimethylene diamine, N-(4-n-heptylphenyl)-N',N'-diethyl-ethylene diamine, N-(4-n-octylphenyl)-N',N'-diethyl-ethylene diamine, and N-(3-chloro-4-fluorophenyl)-N',N'-diethyl-ethylene diamine.

Figures 10, 11, 12, 13:
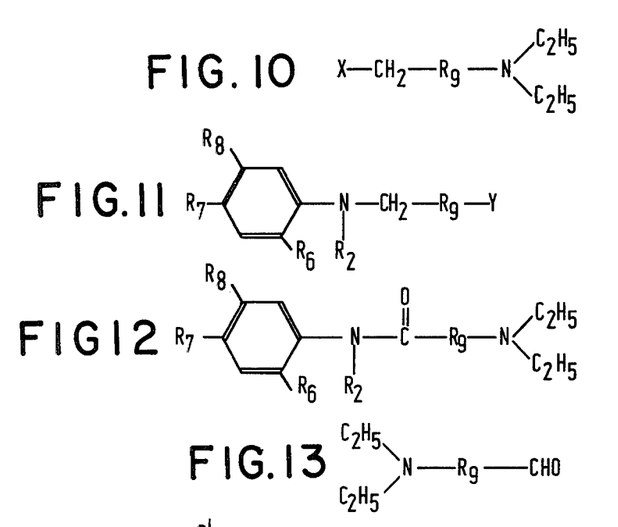

The new compounds according to the invention can be prepared in a manner known per se for the synthesis of related compounds. For example, compounds of the general formula of FIG. 4 can be prepared (a) by reacting a compound of the general formula of FIG. 9 wherein $R_6$, $R_7$ and $R_8$ have the above meanings, with a compound of the general formula of FIG. 10 wherein X is a halogen atom, a tosyloxy group or a hydroxyl group, and $R_9$ has the above meaning, or (b) by reacting a compound of the general formula of FIG. 11 wherein Y is a halogen atom or a tosyloxy group and $R_2$, $R_6$, $R_7$, $R_8$ and $R_9$ have the above meanings, with diethyl amine, or (c) by hydrogenating a compound of the general formula of FIG. 12 wherein $R_2$, $R_6$, $R_7$, $R_8$ and $R_9$ have the above meanings, or (d) by reacting a compound of the general formula of FIG. 13 wherein $R_9$ has the above meanings, under reductive conditions with a compound of the general formula of FIG. 9 wherein $R_2$, $R_6$, $R_7$ and $R_8$ have the above meanings.

Figures 5, 6, 7:
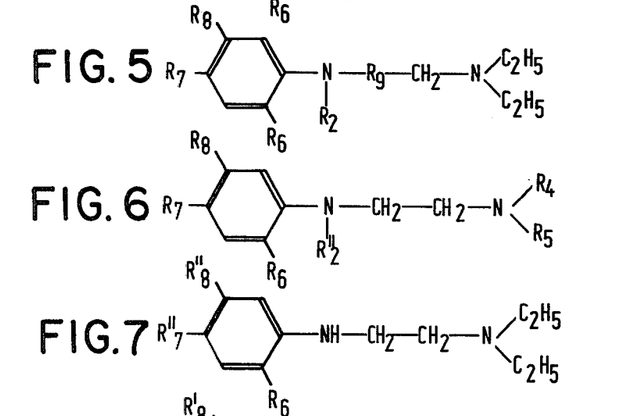
Figures 8, 9:
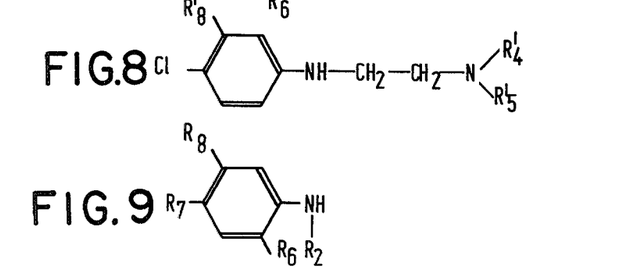
Figure 16:
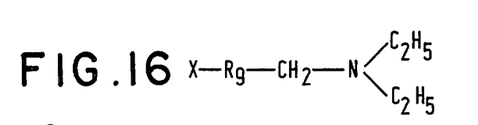
Figures 17, 18:
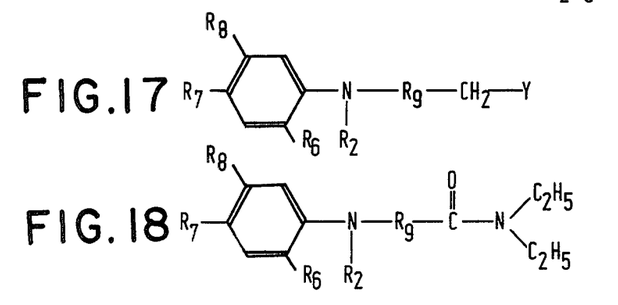
Figures 19, 20:
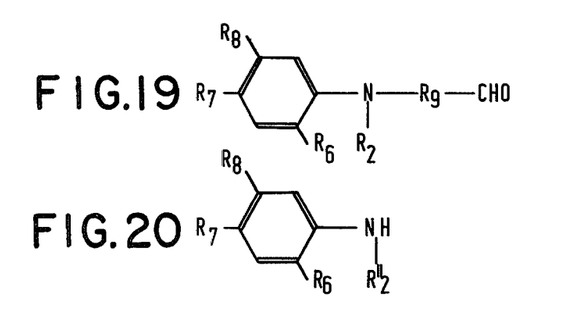
Figure 21:
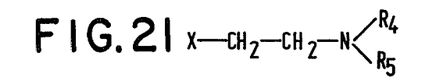
Figure 22:
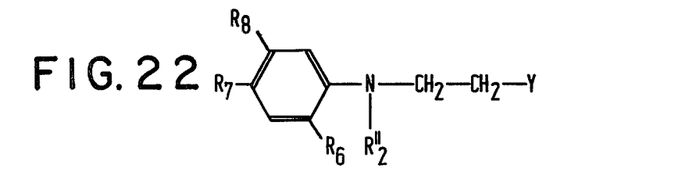
Figure 23:
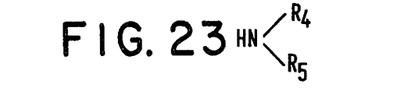
Figure 24:
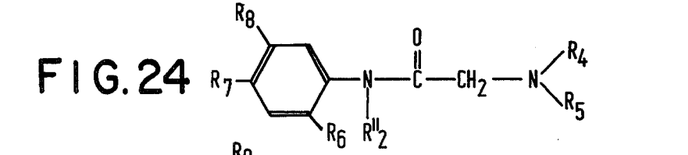
Figure 25:
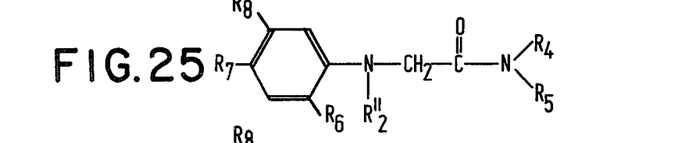
Figure 26:
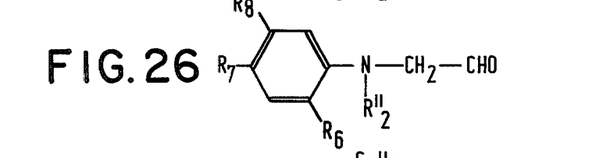
Figure 27:
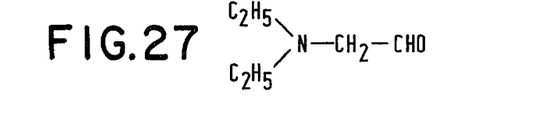
Figure 28:
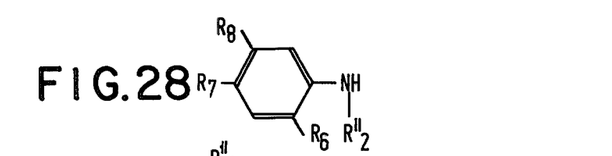

Compounds of the general formula of FIG. 5 can be prepared (a) by reacting a compound of the general formula of FIG. 9 wherein $R_2$, $R_6$, $R_7$ and $R_8$ have the above meanings, with a compound of the general formula of FIG. 16 wherein X and $R_9$ have the above meanings, or (b) by reacting a compound of the general formula of FIG. 17 wherein Y, $R_2$, $R_6$, $R_7$, $R_8$ and $R_9$ have the above meanings, with diethyl amine, or (c) by hydrogenating a compound of the general formula of FIG. 18 wherein $R_2$, $R_6$, $R_7$, $R_8$ and $R_9$ have the above meanings, or (d) by reacting a compound of the general formula of FIG. 19 wherein $R_2$, $R_6$, $R_7$, $R_8$ and $R_9$ have the above meanings, under reductive conditions with diethyl amine Compounds of the general formula of FIG. 6 can be prepared:

(a) by reacting a compound of the general formula of FIG. 20 wherein $R_6$, $R_7$, $R_8$ and $R''_2$ have the above meanings, with a compound of the general formula of FIG. 21 wherein X, $R_4$ and $R_5$ have the above meanings, or (b) by reacting a compound of the general formula of FIG. 22 wherein $R_6$, $R_7$, $R_8$, $R''_2$ and Y have the above meanings, with a compound of the general formula of FIG. 23 wherein $R_4$ and $R_5$ have the above meanings, or (c) by hydrogenating a compound of the general formula of FIG. 24 or 25 wherein $R_4$, $R_5$, $R_6$, $R_7$, $R_8$ and $R''_2$ have the above meanings, or (d) by reacting a compound of the general formula of FIG. 26 wherein $R_6$, $R_7$, $R_8$ and $R''_2$ have the above meanings, under reductive conditions with a compound of the general formula of FIG. 23 wherein $R_4$ and $R_5$ have the above meanings, or (e) by reacting a compound of the general formula of FIG. 27 wherein $R_4$ and $R_5$ have the above meanings, under reductive conditions with a compound of the general formula of FIG. 28 wherein $R_6$, $R_7$, $R_8$ and $R''_2$ have the above meanings.

Figure 29:
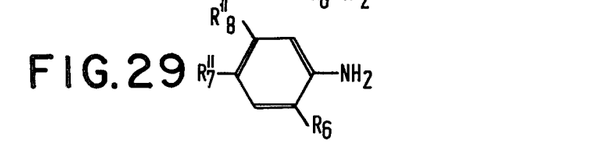
Figure 30:
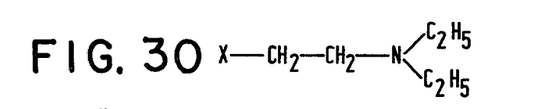
Figure 31:
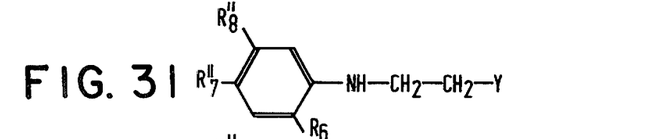
Figure 32:
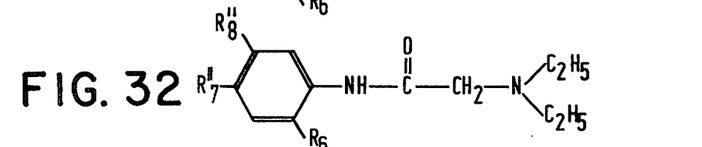
Figure 33:
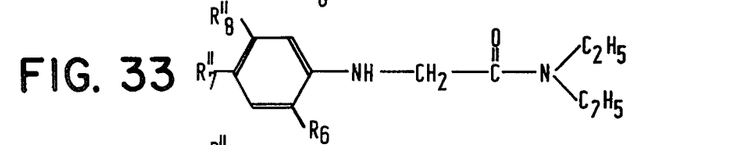
Figure 34:
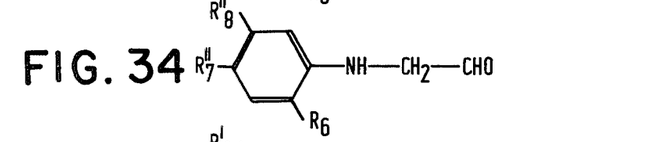

Compounds of the general formula of FIG. 7 can be obtained (a) by reacting a compound of the general formula of FIG. 29 wherein $R_6$, $R''_7$ and $R''_8$ have the above meaning, with a compound of the general formula of FIG. 30 wherein X has the above meaning, or (b) by reacting a compound of the general formula of FIG. 31 wherein $R_6$, $R''_7$, $R''_8$ and Y have the above meanings, with diethyl amine, or (c) by hydrogenating a compound of the general formula of FIG. 32 or 33 wherein $R_6$, $R''_7$ and $R''_8$ have the above meanings, or (d) by reacting a compound of the general formula of FIG. 34 wherein $R_6$, $R''_7$ and $R''_8$ have the above meanings, under reductive conditions with diethyl amine, or (e) by reacting a compound of the formula of FIG. 27 under reductive conditions with a compound of the general formula of FIG. 29 wherein $R_6$, $R''_7$ and $R''_9$ have the above meaning.

Figure 14:
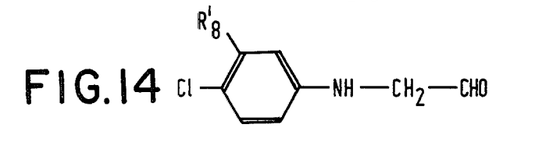
Figure 15:
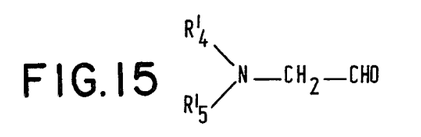
Figure 35:
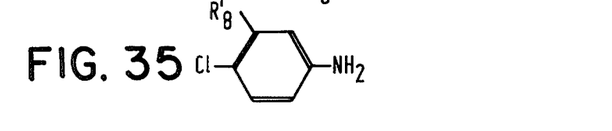
Figure 36:
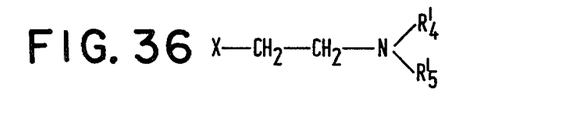
Figure 37:
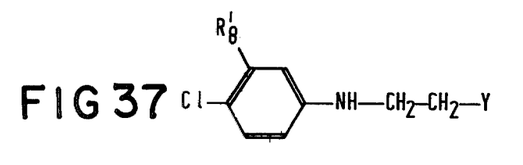
Figure 38:
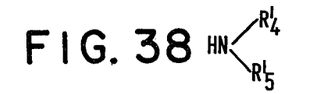
Figures 39, 40:
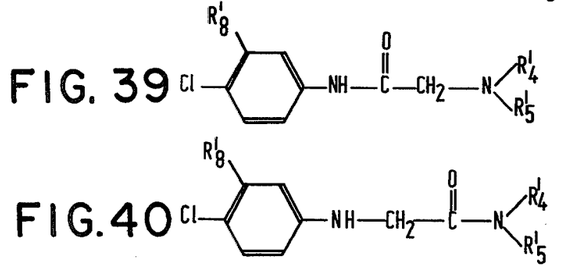

Compounds of the general formula of FIG. 8 can be obtained (a) by reacting a compound of the general formula of FIG. 35 wherein $R'_8$ has the above meaning, with a compound of the general formula of FIG. 36 wherein X, $R'_4$ and $R'_5$ have the above meanings, or (b) by reacting a compound of the general formula of FIG. 37 wherein $R'_8$ and Y have the above meanings, with a compound of the general formula of FIG. 38 wherein $R'_4$ and $R'_5$ have the above meanings, or (c) by hydrogenating a compound of the general formula of FIG. 39 or 40 wherein $R'_4$, $R'_5$ and $R'_8$ have the above meanings, or (d) by reacting a compound of the general formula of FIG. 14 wherein $R'_8$ has the above meaning, under reductive conditions with a compound of the general formula of FIG. 38 wherein $R'_4$ and $R'_5$ have the above meanings, or (e) by reacting a compound of the general formula of FIG. 15 wherein $R'_4$ and $R'_5$ have the above meanings, under reductive conditions with a compound of the general formula of FIG. 35, wherein $R'_8$ has the above meaning.

The reactions mentioned sub (a) and (b), when X represents a halogen atom or a tosyloxy group, are carried out in an inert organic solvent, for example, an aromatic hydrocarbon, at a temperature between 0° C. and the boiling point of the solvent used, preferably at the boiling point of the solvent. These reactions are usually carried out under the influence of a base, for example, sodium carbonate or potassium carbonate or an amine, and/or an alkalimetal iodide. If X is a hydroxyl group, the reaction mentioned sub (a) is carried out by heating the reaction components, whether or not in the presence of an inert organic solvent, preferably under the influence of a strong acid, for example phosphoric acid.

The hydrogenation mentioned sub (c) can be carried out by means of a metal hydride in an inert organix solvent, preferably an ether, for example diethyl ether or tetrahydrofuran at a reaction temperature between room temperature and the boiling point of the solvent used, preferably at the boiling point of the solvent; instead of a metal hydride, diborane may be used as a reductive agent. Alternatively, a catalytic hydrogenation may be carried out for which in addition to hydrogen a catalyst, for example copper chromite or a noble metal catalyst is necessary. Finally, the reduction may be effected by means of sodium borohydride or with zinc and alcohol; in that case the starting amide must first be converted into the corresponding chloroimino compound (Vilsmeier complex).

The reductive amination reactions mentioned sub (d) and (e) are carried out in an inert organic solvent, preferably an alcohol, at a reaction temperature between 0° C. and the boiling point of the solvent used. In this reaction a reductive agent should also be present, for example sodium borohydride, zinc and hydrochloric acid, or hydrogen and a catalyst, for example Raney nickel or a noble metal catalyst.

The invention will now be described in greater detail with reference to the following specific examples.

EXAMPLE 1.

Preparation of N-(3,4-dichlorophenyl)-N-methyl-N',N'-diethylethylene diamine.

5.15 g of N,N-diethylaminoethylchloride. HCl, 7.92 g of 3,4-dichloro-N-methylaniline and 6.35 g of $Na_2CO_3$ were refluxed for 24 hours in 25 ml of toluene. After cooling, a solution of 1.8 g of approximately 90% KOH in 25 ml of water was added. The reaction mixture was extracted with diethyl ether, after which the organic layer was washed with water, dried and filtered. After evaporating the solvent the desired product was obtained in a yield of 10.5 g; the product was identified by means of thin-film chromatography. Purification by means of column chromatography (acetone as an eluent) yielded 4.91 g of an ochrous oil; $n_D^{25} = 1.5511$.

The following compounds were prepared in a corresponding manner;

N-(4-chlorophenyl)-N-methyl-N',N'-diethyl-ethylene diamine; $n_D^{25} = 1.5371$

N-(4-trifluoromethylphenyl)-N',N'-diethyl-ethylene diamine; $n_D^{25} = 1.4829$

N-(4-trifluoromethylphenyl)-N',N'-diethyl-trimethylene diamine, $n_D^{25} = 1.4838$ N-(4-n-butylphenyl)-N',N'-diethyl-ethylene diamine; $n_D^{25} = 1.5112$ N-(4-chlorophenyl)-N-phenyl-N',N'-diethyl-ethylene diamine, identified by means of mass spectrum, N-[4-(4-chlorophenoxy)phenyl]-N',N'-diethyl-ethylene diamine; melting point 47°–50° C., N-(4-chlorophenyl)-N',N'-diethyl-trimethylene diamine; $n_D^{25} = 1.5300$ N-(4-chlorophenyl)-N-ethyl-N',N'-diethyl-ethylene diamine; $n_D^{25} = 1.5327$ N-(4-chlorophenyl)-N-isopropyl-N',N'-diethyl-ethylene diamine; $n_D^{25} = 1.5261$ N-(4-chlorophenyl)-N-isopropyl-N',N'-diethyl-trimethylene diamine; $n_D^{25} = 1.5170$ N-(3,4-dichlorophenyl)-N',N'-diethyl-trimethylene diamine; $n_D^{25} = 1.5392$ N-(4-n-butylphenyl)-N',N'-diethyl-trimethylene diamine; $n_D^{25} = 1.511$ N-(3,4-dichlorophenyl)-N-methyl-N',N'-diethyl-trimethylene diamine, $n_D^{25} = 1.539$ N-(2,4-dimethylphenyl)-N',N'-diethyl-ethylene diamine; $n_D^{25} = 1.518$ N-(2,4-dimethylphenyl)-N',N'-diethyl-trimethylene diamine; $n_D^{25} = 1.5197$ N-(3-chloro-4-fluorophenyl)-N',N'-diethyl-ethylene diamine, $n_D^{25} = 1.5204$ N-(4-cyclohexylphenyl)-N',N'-diethyl-ethylene diamine, $n_D^{25} = 1.5302$ N-(4-n-propylphenyl)-N',N'-diethyl-ethylene diamine, $n_D^{25} = 1.5127$ N-(4-chlorophenyl)-N-ethyl-N',N'-diethyl-trimethylene diamine $n_D^{25} = 1.5305$ N-(4-n-heptylphenyl)-N',N'-diethyl-ethylene diamine, $n_D^{25} = 1.5050$ N-[4-{2-(4-chlorophenyl)ethyl}phenyl]-N',N'-diethyl-ethylene diamine, melting point 67° C., N-(4-n-octylphenyl)-N',N'-diethyl-ethylene diamine, $n_D^{25} = 1.5028$ N-(4-n-nonylphenyl)-N',N'-diethyl-ethylene diamine, $n_D^{25} = 1.5013$ N-(4-trifluoromethoxyphenyl)-N',N'-diethyl-ethylene diamine, $n_D^{25} = 1.467$ N-(4-trifluoromethylsulphonylphenyl)-N',N'-diethyl-ethylene diamine, $n_D^{25} = 1.521$ N-(2,4,5-trimethylphenyl)-N',N'-diethyl-ethylene diamine, $n_D^{25} = 1.5180$ N-(3-chloro-4-fluorophenyl)-N',N'-diethyl-trimethylene diamine, $n_D^{25} = 1.5141$ N-(4-cyclohexylphenyl)-N',N'-diethyl-trimethylene diamine, $n_D^{25} = 1.5260$ N-[4-{2-(4-chlorophenyl)ethyl}phenyl]-N',N'-diethyl-trimethylene diamine, $n_D^{25} = 1.5565$ N-(4-n-hexylphenyl)-N',N'-diethyl-ethylene diamine, $n_D^{25} = 1.5070$ N-(4-tert.butylphenyl)-N',N'-diethyl-ethylene diamine, $n_D^{25} = 1.5122$

EXAMPLE 2

Preparation of N,N-diethyl-2-(3,4-dichloroanilino)propylamine.

2.31 g of N,N-diethyl 2-(3,4-dichloroanilino)propionamide were dissolved in 15 ml of dry tetrahydrofuran. This solution was added dropwise in 5 minutes to a stirred suspension of 0.61 g of lithium-aluminiumhydride in 25 ml of dry tetrahydrofuran. The reaction mixture was refluxed for 6 hours and was left to stand overnight. The next day 0.6 ml of water, 1.5 ml of 15% sodium hydroxide solution and 1.5 ml of water were added successively. After filtration the organic layer was washed with water, dried and filtered. After evaporating the solvent, 2.06 g of the desired product were obtained; identification by means of thin-layer chromatography. The product was purified by means of columnchromatography (acetone as an eluent), after which 1.41 g of an organge oil was obtained; $n_D^{25} = 1.5404$.

The following compounds were prepared in a corresponding manner;

N,N-diethyl-2-(4-chloroanilino)isopropylamine, $n_D^{25} = 1.5268$,

N,N-diethyl-2-(3,4-dichloroanilino)isopropylamine;
  $n_D^{25} = 1.5402$ and
N,N-diethyl-2-(4-chloroanilino)propylamine;
  $n_D^{25} = 1.5270$.

EXAMPLE 3

Preparation of N-(3,4-dichlorophenyl)-N'-tert.butylethylene diamine, hydrochloride.

15.0 g of 2-(3,4-dichloroanilino)ethylchloride, 19.2 g of tert.butylamine and approximately 1 g of sodium iodide were stirred for 26 hours at 90° C. After having been left to stand the weekend over at room temperature, the product was taken up in diethyl ether, washed with successively 2 N sodium hydroxide solution and sodium bicarbonate solution and dried. After evaporating the solvent, 15.85 g of product were obtained, which were purified by column chromatography and then converted into the HCl salt with an alcoholic HCl solution. Melting point 206°–207° C.

N-(3,4-dichlorophenyl)-N'-isopropylethylene diamine, hydrochloride, melting point 179°–180° C., was obtained in a corresponding manner, in which, however, methyl ethyl ketone was used as a solvent for the reaction.

EXAMPLE 4

Preparation of N-(4-chlorophenyl)-N'-methyl-N'-n-butylethylene diamine.

5.70 g of 2-(4-chloroanilino)ethylchloride, 5.28 g of n-butylmethylamine and 6.36 g of $Na_2CO_3$ were refluxed while stirring for approximately 24 hours in toluene as a solvent. After the addition of a solution of 1.80 g of 90% KOH in 15 ml of water the reaction mixture was extracted with diethyl ether. The ether layer was washed with water, dried and filtered. After evaporating the solvent approximately 6 g of product were obtained which was identified by means of thin layer chromatography. The product was purified via the HCl salt, after which 5.21 g of a light-brown oil were obtained; identification by means of N.M.R. spectrum.

EXAMPLE 5

The active substances were processed to compositions by dissolving or dispersing the compounds in water, if desired in the presence of a water-miscible solvent, namely ethoxyethanol, and a polyoxyethylenated ricinus oil as an emulsifier.

The water infested with algae was obtained by adding tap water to algae which were collected from a ditch.

After the addition of a composition according to the invention in various concentrations the algicidal activity was established by determining, 2 weeks after the addition, if, and if so to what extent, the algae were killed. The tests were performed on the following algae: Vaucheria, Cladophora, Mougeotia, Spirogyra, Eudogonium sp. and Enteromorpha.

The results are recorded in the table below: the activity is evaluated as follows:

− = no kill;
+ = kill of 66–80%;
+ + + = kill of 96–100%;
± = kill of 1–65%;
+ + = kill of 81–95%.

| active substance | conc. in mg/l | algicidal activity (after 2 weeks) | | | |
|---|---|---|---|---|---|
| | | Vaucheria | Cladophora | Mougeotia | Eudogonium sp. |
| N-(3,4-dichlorophenyl)- N'-tert.butyl-ethylene- diamine . HCl-salt | 2.0 | +++ | | | |
| | 1.0 | +++ | | | |
| | 0.4 | + | | | |
| N-(3,4-dichlorophenyl)- N'-isopropyl-ethylene- diamine . HCl-salt | 2.0 | +++ | | | |
| | 1.0 | +++ | | | |
| | 0.4 | + | | | |
| N-(4-chlorophenyl)-N',N'- diethyl-ethylenediamine | 2.0 | +++ | +++ | +++ | |
| | 1.0 | +++ | +++ | +++ | |
| | 0.4 | ++ | +++ | +++ | |
| | 0.2 | ± | | | |
| | 0.1 | − | | | |
| N-(3,4-dichlorophenyl)- N',N'-diethyl-ethylene- diamine | 2.0 | +++ | +++ | +++ | +++ |
| | 1.0 | +++ | ± | +++ | +++ |
| | 0.4 | +++ | − | +++ | +++ |
| | 0.1 | ± | | ± | |
| N-phenyl-N',N'-diethyl- ethylene diamine | 2.0 | ++ | | +++ | |
| | 1.0 | ± | | +++ | |
| | 0.4 | ± | | + | |
| N-[4-(4-chlorophenoxy) phenyl]-N',N'-diethyl- ethylene diamine | 2.0 | +++ | | +++ | |
| | 1.0 | ++ | | ± | |
| | 0.4 | ± | | ± | |
| N-(3-chlorophenyl)-N',N'- diethyl-ethylene diamine | 2.0 | +++ | | +++ | |
| | 1.0 | ++ | | +++ | |
| | 0.4 | − | | ++ | |
| N-(4-chlorophenyl)-N'- methyl-N'-n-butyl- ethylene diamine | 2.0 | +++ | | | |
| | 1.0 | +++ | | | |
| | 0.4 | + | | | |

| active substance | conc. in mg/l | algicidal activity (after 2 weeks) | | |
|---|---|---|---|---|
| | | Vaucheria | Cladophora | Eudogonium sp. |
| N-(4-chlorophenyl) 2-piperi- dyl-ethylamine | 2.0 | +++ | | |
| | 1.0 | ++ | | |
| | 0.4 | − | | |
| N-(4-bromophenyl)-N',N'- diethyl-ethylene diamine | 2.0 | +++ | ± | +++ |
| | 1.0 | +++ | ± | +++ |
| | 0.4 | + | − | ++ |
| | 0.2 | ± | | |

-continued

| active substance | conc. in mg/l | | | |
|---|---|---|---|---|
| N-(3-trifluoromethylphenyl)-N',N'-diethyl-ethylene diamine | 0.1<br>2.0<br>1.0<br>0.4 | ±<br>+++<br>+<br>± | ++<br>− | |
| N-(4-chlorophenyl)-N',N'-dimethyl-ethylene diamine | 2.0<br>1.0<br>0.4 | +++<br>+<br>± | | |
| N-(3,4-dichlorophenyl)-N'-ethyl-ethylene diamine . HCl-salt | 2.0<br>1.0<br>0.4 | +++<br>+++<br>− | | |
| N-(3,4-dichlorophenyl)-N',N'-diethyl-trimethylene diamine | 2.0<br>1.0<br>0.4<br>0.2 | +++<br>+++<br>+++<br>± | +++<br>±<br>± | +++<br>+++<br>++ |
| N-(3,4-dichlorophenyl)-N',N'-diethyl-ethylene diamine . HCl-salt | 2.0<br>1.0<br>0.4 | +++<br>+++<br>± | | |
| N-phenyl-N-methyl-N',N'-diethyl-ethylene diamine | 2.0<br>1.0<br>0.4 | ±<br>±<br>− | +++<br>±<br>− | |

| active substance | conc. in mg/l | algicidal activity (after 2 weeks) | | | |
|---|---|---|---|---|---|
| | | Vaucheria | Cladophora | Spirogyra | Eudogonium sp. |
| N-(3,4-dichlorophenyl)-N-methyl-N',N'-diethyl-ethylene diamine | 2.0<br>1.0<br>0.4<br>0.2<br>0.1 | +++<br>+++<br>+++<br>+<br>± | +++<br>+++<br>+++ | | |
| N-(4-chlorophenyl)-N-methyl-N',N'-diethyl-ethylene diamine | 2.0<br>1.0<br>0.4<br>0.2 | +++<br>+++<br>++<br>− | +++<br>+++<br>++ | | ++<br>±<br>± |
| N,N-diethyl 2-(4-chloro-anilino)isopropylamine | 2.0<br>1.0<br>0.4 | +<br>±<br>± | | | |
| N-(4-chlorophenyl)-N-isopropyl-N',N'-diethyl-ethylene diamine | 2.0<br>1.0<br>0.4<br>0.2 | +++<br>+++<br>+ | | | |
| N-(4-trifluoromethylphenyl)-N',N'-diethyl-ethylene diamine | 2.0<br>1.0<br>0.4<br>0.2 | +++<br>+++<br>+++ | | | |
| N-(4-trifluoromethylphenyl)-N',N'-diethyl-trimethylene diamine | 2.0<br>1.0<br>0.4<br>0.2 | +++<br>+++<br>+++ | | | |
| N-(4-chlorophenyl)-N-isopropyl-N',N'-diethyl-trimethylene diamine | 2.0<br>1.0<br>0.4 | +<br>+<br>− | | +++<br>++<br>− | |

| active substance | conc. in mg/l | algicidal activity (after 2 weeks) | | |
|---|---|---|---|---|
| | | Vaucheria | Mougeotia | Spirogyra |
| N-(4-n-butylphenyl)-N',N'-diethyl-ethylene diamine | 2.0<br>1.0<br>0.4<br>0.2 | +++<br>+++<br>++ | | +++<br>+++<br>+ |
| N-(4-methylphenyl)-N',N'-diethyl-ethylene diamine | 2.0<br>1.0 | ++<br>− | ++<br>− | |
| N,N-diethyl 2-(3,4-dichloro-anilino)isopropylamine | 2.0<br>1.0<br>0.4 | +++<br>+++<br>± | | |
| N,N-diethyl 2-(4-chloro-anilino)propylamine | 2.0<br>1.0 | +++<br>− | | |
| N-(4-chlorophenyl)-N-phenyl-N',N'-diethyl-ethylenediamine | 2.0<br>1.0<br>0.4<br>0.2 | +++<br>+++<br>++ | | |
| N-(4-chlorophenyl)-N',N'-diethyl-trimethylene diamine | 2.0<br>1.0<br>0.4 | +++<br>++<br>− | | |
| N,N-diethyl 2-(3,4-dichloro-anilino)propylamine | 2.0<br>1.0<br>0.4<br>0.2 | +++<br>+++<br>++ | | |
| N-(4-chlorophenyl)-N-ethyl-N',N'-diethyl-ethylenediamine | 2.0<br>1.0<br>0.4 | +++<br>+++<br>− | | |

-continued

| active substance | conc. in mg/l | algicidal activity (after 2 weeks) | |
|---|---|---|---|
| | | Vaucheria | Cladophora |
| N-(4-n-butylphenyl)-N',N'-diethyl-trimethylenediamine | 2.0 | +++ | ++ |
| | 1.0 | +++ | + |
| | 0.4 | +++ | − |
| | 0.2 | ± | |
| | 0.1 | − | |
| N-(3,4-dichlorophenyl)-N-methyl-N',N'-diethyl-trimethylenediamine | 2.0 | +++ | ++ |
| | 1.0 | +++ | ++ |
| | 0.4 | +++ | − |
| N-(2,4-dimethylphenyl)-N',N'-diethyl-ethylenediamine | 2.0 | +++ | |
| | 1.0 | + | |
| | 0.4 | ± | |
| N-(3-chloro-4-methylphenyl)-N',N'-diethyl-ethylenediamine . HCl-salt | 2.0 | +++ | + |
| | 1.0 | +++ | − |
| | 0.4 | ++ | |
| N-(1-naphthyl)-N',N'-diethyl-ethylenediamine, oxalate | 2.0 | +++ | |
| | 1.0 | ++ | |
| | 0.4 | ± | |
| N-(2,4-dimethylphenyl)-N',N'-diethyl-trimethylenediamine | 2.0 | +++ | |
| | 1.0 | − | |
| N-(3-chloro-4-fluorophenyl)-N',N'-diethyl-ethylenediamine | 2.0 | +++ | + |
| | 1.0 | +++ | ± |
| | 0.4 | ± | − |
| | 0.2 | − | |
| N-(4-chlorophenyl)-N',N'-diethyl-pentamethylenediamine | 2.0 | +++ | ± |
| | 1.0 | +++ | − |
| | 0.4 | − | |

| active substance | conc. in mg/l | algicidal activity (after 2 weeks) | | |
|---|---|---|---|---|
| | | Vaucheria | Cladophora | Enteromorpha |
| N-(4-cyclohexylphenyl)-N',N'-diethyl-ethylenediamine | 2.0 | +++ | +++ | |
| | 1.0 | +++ | + | |
| | 0.4 | +++ | ± | |
| | 0.2 | +++ | | |
| | 0.1 | ++ | | |
| N-(4-n-propylphenyl)-N',N'-diethyl-ethylenediamine | 2.0 | +++ | + | |
| | 1.0 | +++ | ± | |
| | 0.4 | ++ | − | |
| | 0.2 | + | | |
| | 0.1 | ± | | |
| N-(4-chlorophenyl)-N-ethyl-N',N'-diethyl-trimethylenediamine | 2.0 | ++ | | |
| | 1.0 | − | | |
| N-[4-{2-(4-chlorophenyl)-ethyl}phenyl]-N',N'-diethyl-ethylenediamine | 2.0 | ± | | |
| | 1.0 | ± | | |
| N-(4-n-nonylphenyl)-N',N'-diethyl-ethylenediamine | 2.0 | +++ | | ± |
| | 1.0 | +++ | | − |
| | 0.4 | +++ | | |
| | 0.2 | − | | |
| N-(4-trifluoromethoxyphenyl)-N',N'-diethyl-ethylenediamine | 2.0 | +++ | | +++ |
| | 1.0 | +++ | | ± |
| | 0.4 | ± | | − |
| N-(4-trifluoromethylsulphonylphenyl)-N',N'-diethyl-ethylenediamine | 2.0 | +++ | | ± |
| | 1.0 | + | | − |
| | 0.4 | − | | |
| N-(4-chlorophenyl)-N'-ethyl-piperazine | 2.0 | +++ | ± | |
| | 1.0 | +++ | − | |
| | 0.4 | ± | | |
| N-(2,4,5-trimethylphenyl)-N',N'-diethyl-ethylenediamine | 2.0 | +++ | + | |
| | 1.0 | +++ | + | |
| | 0.4 | +++ | − | |
| | 0.2 | − | | |
| N-(2,4-dichlorophenyl)-N',N'-diethyl-ethylenediamine | 2.0 | +++ | + | |
| | 1.0 | +++ | ± | |
| | 0.4 | +++ | ± | |
| N-(3-chloro-4-fluorophenyl)-N',N'-diethyl-trimethylenediamine | 2.0 | +++ | | |
| | 1.0 | +++ | | |
| | 0.4 | ± | | |
| N-(4-cyclohexylphenyl)-N',N'-diethyl-trimethylenediamine | 2.0 | +++ | +++ | |
| | 1.0 | +++ | ++ | |
| | 0.4 | +++ | ++ | |
| | 0.2 | ++ | | |
| | 0.1 | ± | | |
| N-[4-{2-(4-chlorophenyl)-ethyl}phenyl]-N',N'-diethyl-trimethylenediamine | 2.0 | +++ | ± | |
| | 1.0 | +++ | ± | |
| | 0.4 | +++ | ± | |
| | 0.2 | ± | | |

-continued

| 0.1 | ± |  |
|---|---|---|

EXAMPLE 6

The fish toxicity of the compositions prepared according to example 5 was determined by adding a composition in various concentrations to water, in which zebra fishes or guppies were present. The fish toxicity was determined with reference to mortality figures of the fish after 96 hours. The mortality percentage is stated in the table below.

| active substance | conc. in mg/l | fish toxicity after 96 hours | |
|---|---|---|---|
| | | zebra fishes | guppies |
| N-(4-chlorophenyl)-N',N'-diethyl-ethylenediamine | 5 | 0 | 0 |
| | 3 | 0 | 0 |
| N-(3,4-dichlorophenyl)-N',N'-diethyl-ethylene-diamine | 5 | 90 | 50 |
| | 3 | 60 | 30 |
| | 1 | 40 | |
| N-phenyl-N',N'-diethyl-ethylenediamine | 1 | | 0 |
| N-[4-(4-chlorophenoxy)phenyl]-N',N'-diethyl-ethylenediamine | 1 | | 0 |
| N-(3-chlorophenyl)-N',N'-diethyl-ethylenediamine | 1 | | 0 |
| N-(3,4-dichlorophenyl)-N',N'-diethyl-trimethylenediamine | 3 | 0 | |
| | 1 | 0 | |
| N-phenyl-N-methyl-N',N'-diethyl-ethylenediamine | 5 | 0 | |
| | 3 | 0 | |
| N-(3,4-dichlorophenyl)-N-methyl-N',N'-diethyl-ethylenediamine | 5 | 40 | |
| | 3 | 0 | |
| N-(4-chlorophenyl)-N-methyl-N',N'-diethyl-ethylenediamine | 5 | 90 | |
| | 3 | 0 | |
| | 1 | 0 | |
| N-(4-methylphenyl)-N',N'-diethyl-ethylenediamine | 1 | | 0 |

EXAMPLE 7

N-(4-chlorophenyl)-N',N'-diethyl-ethylenediamine (1) and N-(3,4-dichlorophenyl)-N',N'-diethyl-ethylene diamine (2) were tested in field experiments for algae. For this purpose a liquid composition consisting of 25% by weight of active substance, 10% by weight of emulsifier (polyoxyethylenated ricinus oil) in 65% by weight of ethoxyethanol was sprayed in a ditch containing algae. The ditch contained the following species of algae: Cladophora, Eudogonium and Spirogyra. Some time after the treatment it was established if, and if so to what extent, the algae had been killed by the treatment. For comparison the results are given of an untreated adjacent ditch. The results below are averages of 5 tests; the activity is evaluated arbitrarily between 0 and 10:0=no effect, 10=complete kill.

| Treatment | Dosage in ppm. | Evaluation: days after the treatment | | | |
|---|---|---|---|---|---|
| | | 1 | 2 | 5 | 9 |
| with (1) | 0.2 | 5.0 | 5.0 | 4.0 | 7.0 |
| with (1) | 0.4 | 5.0 | 5.0 | 5.0 | 7.0 |
| with (2) | 0.2 | 4.0 | 4.0 | 4.0 | 7.5 |
| with (2) | 0.4 | 4.0 | 6.0 | 6.0 | 9.0 |
| untreated | — | 0 | 0 | 0 | 0 |

The oxygen content in the dish proved to have undergone no or hardly any influence after the treatment, as appears from the result below:

| Treatment | Dosage in ppm | Oxygen measurement: days after the treatment | | | | |
|---|---|---|---|---|---|---|
| | | 1 | 2 | 5 | 9 | 19 |
| with (1) | 0.2 | 14.9 | 10.8 | 9.8 | 8.2 | 8.9 |
| with (1) | 0.4 | 11.7 | 9.0 | 9.0 | 5.4 | 10.1 |
| untreated | — | 9.4 | 9.6 | 9.8 | 6.9 | 11.9 |

Phytoplankton present in the ditch, inter alia Chlamydomonas, Scenedesmus, Trachetomonas and Melosira, was counted prior to and after the treatment with a composition containing compound (1) in concentrations (of active substance) of 0.5, 1.0 and 2.0 ppm. From these counts it appeared that the treatment had no effect on the number of species in the plankton population and on their density.

EXAMPLE 8

The control of the growth of algae (preventive effect) on walls which are in contact with water ("antifouling") was tested by providing N-(3,4-dichlorophenyl)-N',N'-diethylethylene diamine in a plastics tin closed by a diaphragm and exposing said tin on a raft to sea-water. After approximately 3 months no growth of algae on the disphragm could be established in contrast with a similar tin in which no active substance had been present; the diaphragm of the last-mentioned tin was fully covered with algae after said period.

EXAMPLE 9

In addition to the fish-toxicity, the toxicity with respect to Daphnia magna (water-flea) gives a good indication as to the safety when using the substances in surface waters.

The experiments were carried out under the following conditions:

Experimental animals: *Daphnia magna;* age at the beginning of the test 4–28 hours; 20 animals per test; during the test the animals were not fed; water: 200 ml of fresh tap water; during the repetitions (see hereinafter) 75% thereof was refreshed; temperature 18° C.

The tests were repeated twice. The substances were tested in very high concentrations, namely 5 ppm so as to enable a good distinction between the substances to be tested.

After 48 hours it was determined how many water-fleas had become immobile.

The following average results were obtained.

| active substance | conc. in ppm. | immobility in % |
|---|---|---|
| N-(4-chlorophenyl)-N',N'-diethyl-ethylenediamine | 5 | 28 |
| N-(4-chlorophenyl)-N',N'-diethyl-trimethylenediamine | 5 | 21 |
| N-(4-trifluoromethylphenyl)-N',N'-diethyl-trimethylenediamine | 5 | 16 |
| N-(4-trifluoromethylphenyl)-N',N'-diethyl-ethylenediamine | 5 | 25 |
| N-(4-chlorophenyl)-N-ethyl-N',N'-diethyl-ethylenediamine | 5 | 30 |

-continued

| active substance | conc. in ppm. | immobility in % |
|---|---|---|
| N-(4-chlorophenyl)-N-methyl-N',N'-diethyl-ethylenediamine | 5 | 32 |
| N-(2,4,5-trimethylphenyl)-N',N'-diethyl-ethylenediamine | 5 | 7 |
| N-(4-methylphenyl)-N',N'-diethyl-ethylenediamine | 5 | 30 |
| N-(3-chloro-4-methylphenyl)-N',N'-diethyl-ethylenediamine | 5 | 30 |
| N-(3-chloro-4-fluorophenyl)-N',N'-diethyl-ethylenediamine | 5 | 33 |
| N-(4-trifluoromethoxyphenyl)-N',N'-diethyl-ethylenediamine | 5 | 38 |
| N,N-diethyl 2-(4-chloroanilino)-propylamine | 5 | 39 |
| N-(2,4,5-trichlorophenyl)ethylenediamine (known) | 5 | 100 |
| blank | — | 0 |

The rather high immobility percentage is a result of the high dosage, namely 5 ppm.

From the following experiment it appears that in practice the compounds are not or hardly toxic with respect to water-fleas in lower concentrations of 0.1–1.0 ppm:

The mortality percentage of Daphnia magna in water which was refreshed 3×per week was determined under constant load with an algicidally active composition. The active substance used was N-(4-chlorophenyl)-N',N'-diethyl-ethylenediamine (1). The concentration of active substance in the water was kept constant by adding a calculated quantity of composition to the water each time it was refreshed.

The following results were obtained:

| Treatment | Dosage in ppm. | Mortality percentage after ... weeks | | |
|---|---|---|---|---|
| | | 1 | 2 | 3 |
| with (1) | 0.1 | 0 | 0 | 13 |
| with (1) | 1.0 | 5 | 10 | 37 |
| blank | — | 4 | 15 | 22 |

We claim:
1. An algicidal composition comprising
an algically effective amount of a compound of the formula wherein $R_2'$ is H, methyl, or phenyl,
$R_3'$ is ethylene, trimethylene, or 2-methyl-ethylene,
$R_6$ and $R_8$ are identical or different and are H, Cl, or methyl,
$R_7$ is Cl or methyl, with the provisos that (a) if $R_6$ and $R_8$ are both H, $R_7$ is in addition trifluoromethyl, n-$C_2$-$C_{10}$-alkyl, or cyclohexyl, (b) not all $R_6$, $R_7$, and $R_8$ are Cl, and (c) if $R_6$ and $R_8$ are H and $R_7$ is Cl, $R_3'$ is ethylene, or a salt thereof and
a solid or liquid inert material.

2. The algicidal composition of claim 1 wherein said compound has the formula wherein $R_7'$ is cyclohexyl, trifluoromethyl, or n-butyl.

3. A composition as claimed in claim 1, characterized in that the active constituent is a compound selected from the group consisting of N-(3,4-dichlorophenyl)-N',N'-diethyltrimethylene diamine, N-(4-trifluoromethylphenyl)-N',N'-diethyltrimethylene diamine and N-(2,4,5-trimethylphenyl)-N',N'-diethyl-ethylene diamine.

4. A method of preventing or controlling the growth of algae comprising treating the aqueous locus of said algae with a algicidally effective amount of the composition of claim 1.

5. The method of claim 4 wherein the algicidal composition is employed in a dosage corresponding to 0.12 to 10 kilograms of the active substance per hectare of surface water.

6. The method of claim 4 wherein the algicidal composition is employed in a dosage corresponding to 0.05 to 10 milligrams of the active substance per liter of water.

* * * * *